United States Patent [19]

Szántay et al.

[11] Patent Number: 5,716,986

[45] Date of Patent: Feb. 10, 1998

[54] OXAINDENE DERIVATIVES AND PROCESS FOR THE PREPARATION THEREOF

[75] Inventors: Csaba Szántay; Lajos Novák; Péter Kovács; Klára Gadó; Gábor Gigler; Julianna Takács née Bitai; András Egyed; Dániel Bózsing; György Pirok; Katalin Szemerédi; Margit Csörgő; Sándor Drabant; Gábor Blaskó; Gyula Simig; Gábor Kovács, all of Budapest, Hungary

[73] Assignee: Egis Gyogyszergyar Rt., Budapest, Hungary

[21] Appl. No.: 671,515

[22] Filed: Jun. 27, 1996

[30] Foreign Application Priority Data

Jun. 27, 1995 [HU] Hungary ............... P9501887
Jun. 27, 1995 [HU] Hungary ............... P9501888

[51] Int. Cl.[6] ............... A61K 31/34; C07D 307/91; C07D 307/93
[52] U.S. Cl. ............... 514/468; 549/458; 549/460; 549/461
[58] Field of Search ............... 549/458, 460, 549/461; 514/468

[56] References Cited

U.S. PATENT DOCUMENTS 3,574,627  4/1971  Stern et al. ............... 430/551

FOREIGN PATENT DOCUMENTS 084856  8/1983  European Pat. Off.
869278  12/1986  U.S.S.R.

OTHER PUBLICATIONS

Hosokawa et. al., J. Org. Chem., vol. 43 (11), pp. 2752–2757, 1978.
Beddoes et. al., J. Chem. Soc. Perkin Trans. I, vol. 10, pp. 2670–2676, 1981.
Chemical Abstracts, vol. 110, 165948 (1989).

Primary Examiner—Bernard Dentz
Attorney, Agent, or Firm—Birch, Stewart, Kolasch & Birch, LLP

[57] ABSTRACT

This invention relates to new oxaindene derivatives, a process for the preparation thereof and pharmaceutical compositions comprising the same.

The compounds according to the invention are characterized by the general formula (1)

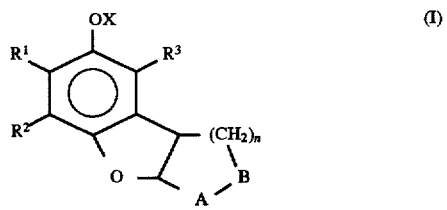

wherein
$R^1$ represents lower $C_{1-4}$ alkyl, lower $C_{1-4}$ alkoxy or lower $C_{3-6}$ cycloalkyl,
$R^2$ stands for hydrogen, lower $C_{1-4}$ alkyl or lower $C_{3-6}$ cycloalkyl,
$R^3$ stands for hydrogen, lower $C_{1-4}$ alkyl, lower $C_{1-4}$ alkoxy or benzyloxy,
X denotes hydrogen, an aliphatic $C_{1-4}$-acyl or benzoyl or naphthoyl group, optionally substituted by 1 or more nitro or $C_{1-4}$-alkoxy group(s) or a group of the formula $R^5R^6N—R^7—$, wherein $R^7$ represents lower $C_{1-4}$ alkylene and $R^5$ and $R^6$ each represent lower $C_{1-4}$ alkyl, or $R^5$ and $R^6$ together with the nitrogen atom to which they are attached form a piperidyl or morpholinyl group,
A and B together form an ethylene or a vinylene group, and n is 1, 2 or 3,
and have a strong 5-lipoxygenase (5-LO) enzyme inhibiting activity.

23 Claims, No Drawings

OXAINDENE DERIVATIVES AND PROCESS FOR THE PREPARATION THEREOF

This invention relates to new oxaindene derivatives, a process for the preparation thereof, pharmaceutical compositions comprising the same, to the use of the said oxaindene derivatives for the treatment of diseases and for the preparation of pharmaceutical compositions suitable for the treatment of diseases.

Tricyclic compounds similar to the compounds according to the invention are provided in the Soviet patent application No. 869,278. The compounds have β-adrenoblocking, hypotensive, spasmolytic and neurodepressive activities.

Benzofurane derivatives fused with a cyclohexene and a cyclopentane ring are described in J. Org. Chem. 1978, 43 (14), 2752–7 and in J. Chem. Soc., Perkin Trans. I, 1981 (10), 2670–6; respectively. No effect is attributed to these compounds.

In the European patent application No. 84,856 tricyclic compounds similar to the compounds according to the invention are described. Ulcus inhibiting and hypotensive activities are attributed to the said compounds.

According to an aspect of the present invention there are provided compounds of general formula (I),

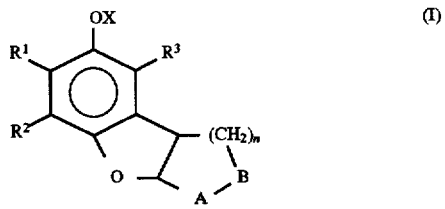

wherein
$R^1$ represents lower $C_{1-4}$ alkyl, lower $C_{1-4}$ alkoxy or lower $C_{3-6}$ cycloalkyl,
$R^2$ stands for hydrogen, lower $C_{1-4}$ alkyl or lower $C_{3-6}$ cycloalkyl,
$R^3$ stands for hydrogen, lower $C_{1-4}$ alkyl, lower $C_{1-4}$ alkoxy or benzyloxy,
X denotes hydrogen, an aliphatic $C_{1-4}$-acyl or benzoyl or naphthoyl group, optionally substituted by 1 or more nitro or $C_{1-4}$-alkoxy group(s) or a group of the formula $R^5R^6N-R^7-$, wherein $R^7$ represents lower $C_{1-4}$ alkylene and $R^5$ and $R^6$ each represent lower $C_{1-4}$ alkyl, or $R^5$ and $R^6$ together with the nitrogen atom to which they are attached form a piperidyl or morpholinyl group,
A and B together form an ethylene or a vinylene group, and n is 1, 2 or 3,
stereoisomers and pharmaceutically acceptable acid addition salts thereof.

The new compounds of general formula (I) are strong inhibitors of the 5-lipoxygenase (5-LO) enzyme.

In a preferred group of the compounds of general formula (I) according to the invention $R^1$, $R^2$ and $R^3$ are independently hydrogen, lower alkyl, X denotes hydrogen, A and B together represent a vinylene group and n is 1 or 2.

In another preferred group of the compounds of general formula (I) according to the invention $R^1$, $R^2$ and $R^3$ are independently hydrogen, lower alkyl, X stands for hydrogen, A and B together form an ethylene group and n is 1 or 3.

Particularly preferred representatives of the compounds according to the invention are the following molecules: cis-4,6,7-trimethyl-2,3,3a,8a-tetrahydro-1H-8-oxacyclopenta[a]indene-5-ol, 1,2,4-trimethyl-4b,6,7,8,9,9a-hexahydro-5H-10-oxabenzo[a]azulene-3-ol and cis-4,6,7-trimethyl-3a,8a-dihydro-3H-8-oxacyclopenta[a]indene-5-ol.

The term "lower" used throughout the specification and claims is intended to mean 1 to 4 carbon atom(s), or in case of the cycloalkyl group 3 to 6 carbon atoms. The term "lower alkyl" refers to straight or branched ones such as methyl, ethyl, n-propyl, isopropyl, n-butyl etc., in which the preferred one may be methyl. The term "lower cycloalkyl" covers cyclic groups containing 3 to 6 carbon atoms (e.g. cyclopropyl, cyclobutyl, cyclopentyl or cyclohexyl). Suitable "lower alkoxy" may include methoxy, ethoxy, propoxy, isopropoxy and the like, in which the preferred one may be methoxy. The term "acyl" covers an aliphatic $C_{1-4}$-acyl or benzoyl or naphthoyl group, optionally substituted by 1 or more nitro or $C_{1-4}$-alkoxy group(s).

According to a further aspect of the present invention there is provided a process for the preparation of the compounds of general formula (I), which comprises
(a) for the preparation of compounds of general formula (I), wherein A and B together form a vinylene group and $R^1$, $R^2$, $R^3$, X and n are as stated above, reacting a hydroquinone derivative of general formula (II),

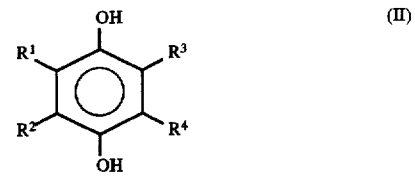

wherein $R^1$, $R^2$ and $R^3$ are as stated above and $R^4$ represents hydrogen or lower alkoxy, with a cycloalkene derivative of general formula (III),

wherein n is as stated above, in a solvent, in the presence of the catalytic amount of a strong acid, and, if desired, subjecting the thus-obtained compound of general formula (I), wherein X represents hydrogen, to acylation or alkylation, or b) for the preparation of compounds of general formula (I), wherein A and B together form an ethylene group,
  b1) subjecting a compound of general formula (I), wherein A and B together form a vinylene group, X stands for hydrogen and $R^1$, $R^2$, $R^3$ and n are as stated above, to catalytic hydrogenation, or
  b2) reacting a hydroquinone derivative of general formula (II), wherein $R^1$, $R^2$ and $R^3$ are as stated above and $R^4$ represents hydrogen, with a cycloalkadiene derivative of general formula (IV)

wherein n is as stated above, in a solvent, in the presence of the catalytic mount of a strong acid,
and, if desired, subjecting the thus-obtained compound of general formula (I), wherein X represents hydrogen, to acylation or alkylation.

and, if possible and desired, converting the base of general formula (I) thus-obtained into an acid addition salt thereof.

According to variant a) of the process according to the invention a hydroquinone derivative of general formula (II) is reacted with a cycloalkene derivative of general formula (III) in a solvent, in the presence of the catalytic mount of a strong acid. As solvent for the reaction anhydrous aprotic solvents, preferably aromatic hydrocarbons (such as benzene, toluene or xylene) or halogenated hydrocarbons (e.g. methylene chloride, chloroform, 1,2-dichloroethane etc.) can be used. The reaction is performed in the presence of the catalytic amount of a strong acid (e.g. p-toluenesulfonic acid, camphorsulfonic acid, benzenesulfonic acid etc., preferably camphorsulfonic acid). One proceeds at an elevated temperature, preferably between 60° C. and 110° C. The thus-obtained compound of general formula (I) can be isolated e.g. by cooling the reaction mixture to room temperature, shaking it with some water, separating the phases, extracting the aqueous phase with an appropriate organic solvent (e.g. dichloromethane), washing and drying the combined organic phases and distilling off the solvent. The thus obtained compound of general formula (I) is optionally purified by crystallization or column chromatography.

According to variant b) of the process according to the invention compounds of general formula (I), wherein A and B together form an ethylene group are produced. According to variant b1) a compound of general formula (I), wherein A and B together form a vinylene group, X stands for hydrogen and $R^1$, $R^2$, $R^3$ and n are as stated above, is subjected to catalytic hydrogenation. As catalyst preferably palladium (e.g. palladium applied onto charcoal) may be used. The catalytic hydrogenation can be performed in a polar solvent (preferably in a lower alcohol, such as methanol), at a temperature between 0° C. and 30° C., under atmospheric pressure or under a slightly elevated pressure. One works preferably at room temperature and under atmospheric pressure. The thus-obtained compound of general formula (I), wherein X stands for hydrogen, is separated from the reaction mixture by filtering off the catalyst, evaporating the filtrate and optionally purifying the residue by recrystallization or column chromatography.

According to variant b2) of the process according to the invention a hydroquinone derivative of general formula (II) is reacted with a cycloalkadiene of general formula (IV). The reaction is carried out in the presence of catalytic amount of a strong acid. For this purpose e.g. p-toluenesulfonic acid, benzenesulfonic acid, camphorsulfonic acid etc. can be used. The reaction is carried out in a solvent, preferably in an anhydrous aprotic solvent. Preferably benzene, toluene, xylene or the mixtures thereof may be used as reaction medium. The reaction is preferably performed at an elevated temperature, preferably at a temperature between 30° C. and 90° C. The thus-obtained compound of general formula (I) containing hydrogen in the place of X can be isolated from the reaction mixture e.g. by cooling the latter to room temperature, washing, drying and evaporating it. The residue may optionally be purified by recrystallization or column chromatography.

The compound of general formula (I) containing a hydrogen atom in the place of X obtained according to any of the reactions specified above is optionally acylated or alkylated. The acylation can be carried out with organic carboxylic acids containing the acyl group to be introduced, or with functional derivatives thereof (e.g. acid halides, acid anhydrides etc.). As acid halide preferably an acid chloride is applied.

If a carboxylic acid is used as an acylating agent, the reaction is preferably carried out in an aprotic dipolar solvent (such as dimethylformamide), in the presence of a condensing agent. As condensing agent e.g. compounds of carbodiimide type (preferably dicyclohexylcarbodiimide) may be used.

The acylation carried out with acid anhydrides can be performed in apolar aprotic solvents (such as ether, dioxane, benzene, chloroform, dichloromethane etc.). The reaction is carried out in the presence of an acid binding agent (e.g. alkali carbonates, sodium hydride or organic bases). Certain organic bases (e.g. pyridine) can serve both as solvents and as acid binding agents.

The acylation carried out with acid halides—preferably acid chlorides—can be performed in an inert organic solvent. As reaction medium aliphatic ethers (e.g. diethyl ether, tetrahydrofurane etc.), or optionally halogenated aliphatic hydrocarbons (e.g. dichloromethane) can be used, but the acid binding agent (e.g. pyridine) may serve as reaction medium as well.

The reaction temperature may vary between wide ranges, but it is preferably to carry out the reaction at room temperature. It is preferably performed in the presence of an acid binding agent. For this purpose organic tertiary bases (e.g. triethylamine, pyridine, N-methylmorpholine etc.) can be used. In certain cases the organic bases may serve as solvents and acid binding agents as well.

The alkylation of the compounds of general formula (I) containing a hydrogen atom in the place of X can be carried out with $R^5R^6$-N-alkyl halides, wherein $R^5$ and $R^6$ are as stated above. The alkylation is preferably performed in the presence of a base (e.g. an alkali hydroxide, alkali carbonate, alkali alkoxide, sodium hydride or an organic base).

The compounds of general formula (I), wherein X denotes a group of the formula $R^5R^6$—N—$R^7$, can form acid addition salts with pharmaceutically acceptable acids. For this purpose inorganic acids (e.g. hydrohalides, such as hydrochloric acid or hydrobromic acid, sulfuric, phosphoric or perhaloacids, such as perchloric acid), organic carboxcylic acids (e.g. fumaric, acetic, propionic, glycolic, maleic, hydroxymaleic, ascorbinic, citric, malic, salicylic, lactic, cinnamic, benzoic, phenylacetic, p-aminobenzoic, p-hydroxybenzoic, p-aminosalicylic acid etc.), alkylsulfonic acids (e.g. methanesulfonic ethanesulfonic acid), or arylsulfonic acids (e.g. p-toluenesulfonic, p-bromophenylsulfonic, naphtylsulfonic, sulfanilic acid) may be used.

The starting compounds of general formulae (II), (III) and (IV) used for the preparation of the compounds of general formula (I) are known. They are available from the commerce, or can be prepared as described according to the following publications: W. Baker: Journal of Chemical Society 1941, 662; L. N. Owen et al.: ibid. 1952, 4035, E. Knoevenagel et al.: Berichte, 34, 3993 (1901), J. E. Backvall et al.: Journal of Organic Chemistry 49, 4619 (1984).

The new compounds of general formula (I) are strong inhibitors of the 5-lipoxygenase (5-LO) enzyme. They are more effective by one or two order(s) of magnitude than AA-861, the well-known selective 5-LO inhibitor. The 5-lipoxygenase inhibitors effective both in vitro and in vivo can be used for the treatment of diseases of allergy (e.g. allergic rhinitis), diseases of the joints (e.g. rheumatoid arthritis), diseases of the gastro-intestinal tract (e.g. ulcerous colitis), asthma and some skin disorders (e.g. psoriasis).

The efficacy of the new compounds is demonstrated by the following experiments:

1. Measurement of 5-LO enzyme activity in cell free system prepared from human leukocytes The enzyme activity was measured according to the modified method of Ochi et al. [K. Ochi, T. Yoshimoto, S. Yamamoto, K. Taniguchi, T. Miyamoto: Arachidonate 5-lipoxygenase of guinea pig peritoneal polymorphonuclear leukocytes, J. Biol. Chem. 258, 5754–5758 (1983)]. The principle of the method is as follows: in in vitro systems, during the reaction catalysed by 5-LO 5-hydroxyperoxy-6, 8,11,14-eicosatetraenoic acid (5-HPETE) is formed from arachidonic acid, then it is transformed to 5-hydroxy-6,8, 11,14-eicosatetraenoic acid (5-HETE). Both 5-HPETE and 5-HETE have absorption maximum at 236 nm, therefore it is possible to determine the activity of 5-LO enzyme by measuring the change of absorption at 236 nm. 5-LO was prepared from human polymorphonuclear leukocytes by a simple purification procedure. The cells were washed and lysed by a sonic disintegrator. The lysate was centrifuged and the enzyme in the cytosol was partially purified by ammonium sulphate fractionation (the enzyme precipitates at 50% saturation). The reaction mixture (50 mM tris-HCl pH=7.5, 2mM $CaCl_2$, 0.1 mM ATP, 0.02 mM arachidonic acid) was incubated at 37° C. for 5 minutes. The reaction was started with the addition of arachidonic acid and stopped by the addition of 10 mM of citric acid. The thus-obtained 5-HPETE and 5-HETE were extracted with a 6:4 mixture of diethyl ether and hexane and the absorption of the organic phase was measured by spectrophotometry at 238 nm.

2. Determination of 5-LO enzyme activity of human leukocytes by measuring their leukotriene $B_4$ production The method of Mia et al. was applied [H. Mita, Y. Yui and T. Shida: Effect of AA-861, a 5-lipoxygenase inhibitor on leukotriene synthesis in human polymorphonuclear leukocytes and on cyclooxygenase and 12-lipoxygenase activities in human platelets, Allergy 41, 493–498, (1986)]. The principle of the experiment is as follows: the calcium ionophore A-23187 induces the synthesis and the release of $LTB_4$ by human polymorphonuclear leukocytes. The amount of $LTB_4$ released into the incubation medium reflects the 5-LO enzyme activity of the intact cells. The incubation medium was Hank's balanced medium (HBBS) supplemented with 17 mM of Tris-HCl (pH 7.2), 1.22 mM of $CaCl_2$, 1 mM of $MgCl_2$, 0.001 mM of A-23187 and $10^4$ PMN leukocyte per ml reaction mixture. The reaction was started with the addition of ionophore then incubated at 37° C. for 15 minutes. The reaction was stopped by adding 5 mM of EDTA and by chilling the samples in an ice bath. The samples were centrifuged and the amount of $LTB_4$ in the supernatant was determined by radioimmunoassay (RIA).

3. Ear oedema induced by arachidonic acid in mice

Inflammation of ear was induced by arachidonic acid using a modified version of the procedure described by Young et al. [Young, J. M., Spires, D. A., Bedord, C. J., Wagner, B., Ballaron, S. J., De Young, L. M.: The mouse ear inflammatory response to topical arachidonic acid, J. Invest. Dermatol. 82,67–371 (1984)]. The experiments were carried out in female mice from the NMRI strain weighing 25 to 30 g (8 animals/groups). Drugs were applied topically in acetone or ethanol by an automatic pipette in 10 μl volumes to both the inner and outer surfaces of the ear. 30 minutes after drug or vehicle administration both sides of the left ear were brushed with 3 mg of arachidonic acid in 20 μl of acetone and both sides of the right ear were treated with 20 μl of acetone only. 60 minutes later the animals were killed by aether, then a disk of 7 mm diameter was cut off both ears. The mass of each disk was measured by an analytical scale and the mean of the difference of the left and right ears was calculated for every group. $ID_{50}$ values were determined by plotting the log-dose versus percentage response as compared to vehicle-treated animals.

4. PAF induced anaphylactic shock test in mice

A modification of the method of Young et al. [Young, J. M., Maloney, P. J., Jubb, S. N. and Clark, J. S.: Pharmacological investigation of the mechanism of platelet-activating factor mortality in the mouse, Prostaglandins 30, 545–551 (1985)] was used. The experiments were carried out in male NMRI mice weighing 20–25 g (10 animals/group). The test compounds were suspended in 0.4% methyl cellulose and administered intraperitoneally in a volume of 10 ml/kg. The mice of the control group received only vehicle. 30 minutes later the animals received intravenous PAF in a dose of 100 μg/kg (5 ml/kg). Mortality was determined one hour after PAF administration. Every experiment was repeated three times (n=30). The ratio of mortality of the treated animals was compared to that of the control mice. $ID_{50}$ values were calculated by linear regression analysis.

The results are shown in the following Table. As reference compounds phenidone (1-phenyl-3-pyrazolidinone), AA-861 [2-(12-hydroxy-5,10-dodecadiinyl)-3,5,6-trimethyl-p-benzoquinone) and NDGA (nordihydroguaiaretic acid, 1,4-bis(3,4-dihydroxyphenyl)-2, 3-dimethylbutane) were applied.

| Com-pound (No. of Example) | Arachidonic acid ear oedeme in mice $ID_{50}$ mg/ear | PAF lethality in mice $ID_{50}$ mg/kg | 5-lipoxygenase enzyme inhibition | |
|---|---|---|---|---|
| | | | direct $IC_{50}$ M/l | in whole cell $IC_{50}$ M/l |
| 4 | | 65.2 | $1.2 \times 10^{-6}$ | $3.0 \times 10^{-7}$ |
| 2 | 0.18 | 16.2 | $3.9 \times 10^{-7}$ | $5.0 \times 10^{-8}$ |
| 6 | 0.23 | 100 | $1.2 \times 10^{-6}$ | |
| 8 | | 45.0 | $4.9 \times 10^{-7}$ | |
| 10 | 0.16 | 22.5 | $9.9 \times 10^{-8}$ | $7.0 \times 10^{-8}$ |
| 3 | — | — | $5.5 \times 10^{-6}$ | $5.0 \times 10^{-7}$ |
| 1 | | 51.7 | $7.4 \times 10^{-8}$ | $6.8 \times 10^{-7}$ |
| 5 | 0.18 | — | $2.7 \times 10^{-6}$ | $3.0 \times 10^{-7}$ |
| 7 | 0.11 | 27.3 | $1.7 \times 10^{-6}$ | $3.0 \times 10^{-7}$ |
| 23 | | 23.2 | $5.4 \times 10^{-7}$ | $1.4 \times 10^{-7}$ |
| AA-861 | 0.13 | 58.9 | $4.1 \times 10^{-6}$ | $1.1 \times 10^{-6}$ |
| Phenidone | 0.18 | 14.2 | $3.3 \times 10^{-6}$ | $6.3 \times 10^{-7}$ |
| NDGA | >1.0 | 29.2 | $2.1 \times 10^{-7}$ | $1.4 \times 10^{-7}$ |

As it can be seen from the above Table, the effect of some compounds according to the invention is superior to that of the selective 5-lipoxygenase enzyme inhibitor AA-861 in these tests, while their activities are comparable to those of the dual inhibitors phenidone and NDGA.

According to a further aspect of the present invention there are provided pharmaceutical compositions comprising as active ingredient a compound of general formula (I) or a pharmaceutically acceptable acid addition salt thereof in admixture with suitable inert solid or liquid pharmaceutical carriers.

The pharmaceutical compositions of the present invention can be prepared by methods known per se by admixing the active ingredient with suitable inert, non-toxic, solid or liquid carriers and bringing the mixture to galenic form.

It is preferred to finish the compounds of general formula (I) to tablets or dragées, but they can be administered in form of solution or suspension, too. The daily dose is generally 1 to 800 mg, preferably 10 to 500 mg.

According to a further aspect of the present invention there is provided the use of the compounds of general formula (I) or a pharmaceutically acceptable acid addition salt thereof for the preparation of pharmaceutical compositions suitable particularly for the treatment of diseases of allergy, diseases of the joints, asthma, diseases of the gastrointestinal tract and skin disorders.

According to a still further aspect of the present invention there is provided a method of antiallergic, antiarticular, antiulceric and antiasthmatic treatment, which comprises administering to a patient an effective amount of a compound of general formula (I) or a pharmaceutically acceptable acid addition salt thereof.

Further details of the present invention are to be found in the following Examples without limiting the scope of protection to the said Examples.

EXAMPLE 1 cis-4,6,7-Trimethyl-3a,8a-dihydro-3H-8-oxacyclopenta[a] indene-5-ol (I: $R^1=R^2=R^3=Me$, X=H, A+B=vinylene, n=1)

To a suspension of 35.0 g (0.23 mole) of trimethylhydroquinone) (II: $R^1=R^2=R^3=Me$, $R^4=H$) and 25.0 g (0.25 mole) of cis-4-cyclopentene-1,3-diol (III: n=1) in 300 ml of anhydrous toluene 2.0 g of D-camphor-10-sulfonic acid are added, and the mixture is stirred at a temperature of 70° C. for 40 hours. Then it is cooled, the separated crystals are filtered off and recrystallized from ethanol. Thus 25 g (50.3%) of white needle crystals are obtained. M.p.: 140° C.

$^1$H-NMR (CDCl$_3$): 2.10 (3H, s, CH$_3$), 2.12 (3H, s, CH$_3$), 2.17 (3H, s, CH$_3$), 2.52 and 2.92 (2H, m, CH$_2$), 4.08 (1H, m, CH), 4.16 (1H, s, OH), 5.79 (1H, m, CH), 5.91 (1H, m, CH═), 6.00 (1H, m, CH═).

EXAMPLE 2 cis-4,6,7-Trimethyl-2,3,3 a,8a-tetrahydro-1H-8-oxacyclopenta[a]indene-5-ol (I: $R^1=R^2=R^3=Me$, X=H, A+B=ethylene, n=1)

a) 4.0 g of the product prepared according to Example 1 are dissolved in 300 ml of anhydrous methanol and hydrogenated using as catalyst 0.2 g of 10% palladium on charcoal. When the theoretical amount of hydrogen has been taken up (450 ml, 45 minutes) the catalyst is filtered off, the filtrate is evaporated and the residue is recrystallized from ethanol. Thus 3.5 g (86%) of white crystalline product are obtained.

M.p.: 141° C.

$^1$H-NMR (CDCl$_3$): 1.5–1.8 (5H, m, 5H of the 3CH$_2$ group), 1.8–2.0 (1H, m, H of the CH$_2$ group), 2.09 (3H, s, CH$_3$), 2.12 (3H, s, CH$_3$), 2.16 (3H, s, CH$_3$), 3.76 (1H, m-t, J=7 Hz, CH—O).

b) To a solution of 15.2 g (0.1 mole) of trimethylhydroquinone (II: $R^1=R^2=R^3=Me$ and $R^4=H$) and 7.26 g (0.11 mole) of 1,3-cyclopentadiene (IV: n=1) in 225 ml of anhydrous toluene and 75 ml of anhydrous ether 3.8 g (22 mmoles) of p-toluenesulfonic acid are added, and the mixture is heated in an oil bath of 70° C. for 14 hours. Then it is cooled, 200 ml of ether are added to it, washed with water, dried, the solvent is distilled off and the residue is recrystallized from methanol. Thus 13.2 g (60.5%) of white crystalline product are obtained.

M.p.: 141° C.

EXAMPLE 3 cis-6,7-Dimethyl-3a,8a-dihydro-3H-8-oxacyclopenta[a] indene-5-ol (I: $R^1=R^2=Me$, $R^3=X=H$, A+B=vinylene, n=1)

To a suspension of 11.5 g (83 mmoles) of 2,3-dimethylhydroquinone (II: $R^1=R^2=Me$, $R^3=R^4=H$) and 8.34 g (83 mmoles) of cis-4-cyclopentene-2,3-diol (III: n=1) in 90 ml of anhydrous toluene 0.9 g of D-camphor-10-sulfonic acid is added, and the mixture is stirred at a temperature of 70° C. for 40 hours. Then it is cooled, diluted with 400 ml of ethyl acetate and washed with 200 ml of water. The aqueous phase is extracted with 100 ml of ethyl acetate, the organic phases are combined and washed with water and saturated sodium chloride solution, dried and the solvent is distilled off. The residue is purified by column chromatography (Kieselgel G., hexane:acetone 10:1). Thus 5.65 g (34%) of white needle crystals are obtained.

M.p.: 159° C.

$^1$H-NMR (CDCl$_3$): 2.11 (6H, s, 2CH$_3$), 2.52 and 2.88 (2H,m, CH$_2$), 3.8 (1H, s, OH), 4.0 (1H, m, CH), 5.76 1H, m, CH—O), 5.84 (1H, m, CH═), 5.98 (1H, m, CH═), 6.48 (1H, s, aromatic pr.).

EXAMPLE 4 cis-6,7-Dimethyl-2,3,3a,8a-tetrahydro-1H-8-oxacyclopenta [a]indene-5-ol (I: $R^1=R^2=Me$, $R^3=X=H$, A+B=ethylene, n=1)

a) 3.0 g (15 mmoles) of the product prepared according to Example 3 are hydrogenated in 150 ml of ethanol using 0.2 g of 5% palladium on charcoal catalyst. When the theoretical amount of hydrogen has been taken up (360 ml, 45 minutes) the catalyst is filtered off, the solvent is distilled off, and the residue is crystallized from ethanol. Thus 1.9 g (63%) of white crystalline product is obtained.

M.p.: 142° C.

$^1$H-NMR (CDCl$_3$): 1.5 (1H, m, one H of CH$_2$), 1.6–1.9 (4H, m, 2CH$_2$), 2.05 (1H, m, one H of CH$_2$), 3.77 (1H, t+d, J=7 and 1 Hz, CH), 4.4 (1H, s, OH), 5.20 (1H, m-t, J=6 Hz, CH—O), 6.46 (1H, s, aromatic pr.).

b) 13.8 g (0.11 mole) of 2,3-dimethylhydroquinone (II: $R^1=R^2=Me$, $R^3=R^4=H$) and 7.26 g (0.11 mole) of cis-1,3-cyclopentadiene (IV: n=1) are dissolved in the mixture of 75 ml of anhydrous ether and 225 ml of anhydrous toluene, 3.8 g (22 mmoles) of p-toluenesulfonic acid are added to the solution, and the reaction mixture is heated in an oil bath of 80° C. for 16 hours. The mixture is then cooled, diluted with 200 ml of ether, washed with water, dried and the solvent is distilled off. The residue is recrystallized from ethanol. Thus 10.3 g (50.5%) of white crystalline product are obtained.

M.p.: 142° C.

EXAMPLE 5 cis-6-Methoxy-3a,8a-dihydro-3H-8-oxacyclopenta[a] indene-5-ol (I: $R^1=MeO$, $R^2=R^3=X=H$, A+B=vinylene, n=1).

To a solution of 8.0 g (47.1 mmoles) of 2,5-dimethoxyhydroquinone (II: $R^1=R^4=MeO$, $R^2=R^3=H$) and 5.0 g (51 mmoles) of 4-cyclopentene-1,3-diol (III: n=1) in 100 ml of anhydrous toluene 0.5 g of D-camphor-10-sulfonic acid is added, and the reaction mixture is stirred under argon atmosphere at a temperature of 70° C. for 6 hours. Then it is cooled, the separated by-product (2,5-dimethoxyquinone) is filtered off, the filtrate is evaporated, the residue is purified by column chromatography and recrystallized from hexane. Thus 1.3 g (28%) of white crystalline product is obtained.

M.p.: 116°–118° C.

$^1$H-NMR (CDCl$_3$): 2.52 and 2.86 (2H, m, CH$_2$), 3.81 (3H, s, OCH$_3$), 4.00 (1H, m, CH), 5.25 (1H, s, OH), 5.79 (1H, m, CH—O), 5.82 (1H, m, CH═), 6.00 (1H, m, CH═), 6.38 (1H, s, aromatic pr.), 6.72 (1H, m, aromatic pr.).

EXAMPLE 6 cis-6-Methoxy-2,3,3a,8a-tetrahydro-1H-8-oxacyclopenta[a] indene-5-ol (I: R=MeO, $R^2=R^3=X=H$, A+B=ethylene, n=1)

a) The solution of 3.6 g (19 mmoles) of the product prepared as specified in Example 5 in 200 ml of methanol is subjected to hydrogenation using as catalyst 1.0 g of 5% palladium applied on charcoal. When the theoretical amount of hydrogen has been taken up (460 ml, 20 minutes) the catalyst is filtered off, the filtrated is evaporated and the residue is subjected to chromatography on a short column (Kieselgel 60, hexane-acetone 10:0.3). Thus 0.7 g (19%) of white crystalline product is obtained. M.p.: 100°–103° C.

$^1$H-NMR (CDCl$_3$): 1.49 (1H, m, CH$_2$), 1.6–1.9 (4H, m, 2CH$_2$), 2.03 (1H, m, CH$_2$), 3.76 (1H, m-t, J=8 Hz, CH), 3.81 (3H, s, OCH$_3$), 5.16 (1H, s, OH), 5.22 (1H, m-t, O—CH), 6.32 (1H, s, aromatic pr.), 6.68 (1H, s, aromatic pr.).

b) 5.0 g (36 mmoles) of 2-methoxyhydroquinone (II: R$^1$=MeO, R$^2$=R$^3$=R$^4$=H) and 7.0 g of cis-1,3-cyclopentadiene (IV: n=1) are dissolved in the mixture of 60 ml of anhydrous toluene and 20 ml of ether, 5.0 g of D-camphor-10-sulfonic acid are added to the solution, and it is stirred at a temperature of 40° C. for 24 hours. Then it is cooled, the separated crystals are filtered off, the solvent is distilled off and the residue is purified by column chromatography. Thus 1.0 g (15%) of colourless oil is obtained.

TLC: R$_f$=0.6 (hexane-acetone 10:4).

EXAMPLE 7 cis-6-Ethoxy-3a,8a-dihydro-3H-8-oxacyclopenta[a]indene-5-ol (I: R$^1$=EtO, R$^2$=R$^3$=X=H, A+B-vinylene, n=1)

To a mixture of 14.5 g (73 mmoles of 2,5-diethoxyhydroquinone (II: R$^1$=R$^4$=EtO, R$^2$=R$^3$=H), 7.9 g (81 mmoles) of cis-4-cyclopentene-1,3-diol (III: n=1) in 140 ml of anhydrous toluene 0.7 g of D-camphor-10-sulfonic acid is added, and the mixture is stirred under argon atmosphere at a temperature of 70° C. for 30 hours. Then it is cooled, the separated 2,5-diethoxy-1,4-benzoquinone is filtered off, the mother liquor is evaporated, the residue is purified by column chromatography (Kieselgel, hexane:acetone 5:0.2) and recrystallized from hexane. Thus 4.1 g (51.5%) of colourless crystalline product are obtained. M.p.: 94°–96° C.

$^1$H-NMR (CDCl$_3$): 1.40 (3H, t, J=6 Hz, CH$_3$), 2.52 and 2.86 (2H, m, CH$_2$), 4.02 (3H, m, CH and CH$_2$—O), 5.28 (1H, s, OH), 5.79 (1H, m, CH—O), 5.82 (1H, m, CH=), 6.00 (1H, m, CH=), 6.38 (1H, s, aromatic pr.), 6.72 (1H, s, aromatic pr.).

EXAMPLE 8 cis-6-Ethoxy-2,3,3a,8a-tetrahydro-1H-8-oxa-cyclopenta[a]indene-5-ol (I: R$^1$=EtO, R$^2$=R$^3$=X=H, A+B=ethylene, n=1)

A solution of 4.0 g (18.3 mmoles) of the product prepared as specifed in Example 7 in 200 ml of anhydrous methanol is subjected to hydrogenation using 1.0 g of 5% palladium on charcoal catalyst. When the theroetical amount of hydrogen has been taken up (440 ml, 20 minutes) the catalyst is filtered off, the solvent is distilled off and the residue is recrystallized from hexane. Thus 2.0 g (50%) of white crystalline product are obtained.

M.p.: 94°–96° C.

$^1$H-NMR (CDCl$_3$): 1.42 (3H, t, J=6.5 Hz, CH$_3$), 1.48 (1H, m, CH$_2$), 1.6–1.9 (4H, m, 2CH$_2$), 2.04 (1H, m, CH$_2$), 3.77 (1H, m, J=8 Hz and 2.5 Hz, CH), 4.03 (2H, q, J=6.5 Hz, OCH$_2$), 5.22 (1H, m, J=8 Hz, O—CH), 5.26 (1H, s, OH), 6.30 (1H, s, aromatic pr.), 6.69 (1H, s, aromatic pr.).

EXAMPLE 9 cis-1,2,4-Trimethyl-4b,6,7,9a-tetrahydro-5H-10-oxabenzo[a]azulene-3-ol (I: R$^1$=R$^2$=R$^3$=Me, X=H, A+B=vinylene, n=3)

To a solution of 10.0 g (66 mmoles) of trimethylhydroquinone (II: R$^1$=R$^2$=R$^3$=Me, R$^4$=H) and 14.0 g (0.109 mole) of 2-cycloheptene-1,4-diol (III: n=3) in 150 ml of anhydrous toluene 2.0 g of p-toluenesulfonic acid are added, and the mixture is stirred at a temperature of 75° C. for 6 hours. Then it is cooled, 100 ml of ether are added to it, washed with water and saturated sodium chloride solution, dried and the solvent is distilled off. The residue is purified by column chromatography (Kieselgel 60, hexane:ether 1:1). Thus 4.8 g (30%) of white solid substance are obtained.

$^1$H-NMR (CDCl$_3$): 1.5–1.9 (6H, m, 3CH$_2$), 2.02 (6H, s, 2CH$_3$), 2.08 (3H, s, CH$_3$), 3.25 (1H, m, CH), 4.18 (1H, s, OH), 5.22 (1H, m, CH—O), 5.4–6.2 (2H, m, CH=CH).

EXAMPLE 10

1,2,4-Trimethyl-4b,6,7,8,9,9a-hexahydro-5H-10-oxabenzo[a]azulene-3-ol (I: R$^1$=R$^2$=R$^3$=Me, X=H, A+B=ethylene, n=3)

a) 3.0 g (12.3 mmoles) of the compound prepared as specified in Example 9 are hydrogenated in 100 ml of methanol using 0.1 g of 10% palladium on charcoal catalyst. When the calculated amount of hydrogen has been taken up (300 ml, 1 hour) the catalyst is filtered off, the solvent is distilled off in vacuo and the residue is crystallized from hexane. Thus 1.8 g (59%) of white crystalline product is obtained.

M.p.: 112°–114° C.

$^1$H-NMR (CDCl$_3$): 1.28–1.95 (9H, m, 9H of 5CH$_2$), 2.11 (3H, s, CH$_3$), 2.13 (3H, s, CH$_3$), 2.15 (3H, s, CH$_3$), 2.25 (1H, m, one H of CH$_2$), 3.33 (1H, m, CH), 4.16 (1H, s, OH), 4.79 (1H, m, CH—O).

b) To a suspension of 24.73 g (0.16 mole) of trimethylhydroquinone (III: R$^1$=R$^2$=R$^3$=Me, R$^4$=H) and 17.0 g (0.18 mole) of 1,3-cycloheptadiene (IV: n=3) in 250 ml of anhydrous toluene 2.0 g of p-toluenesulfonic acid are added, and the mixture is stirred at a temperature of 70° C. for 16 hours. Then it is cooled, diluted with 250 ml of ether, washed with water, dried, the solvent is distilled off and the residue is crystallized from a mixture of hexane and ether. Thus 9.8 g (24.5%) of white crystalline product are obtained. M.p.: 112°–114° C.

EXAMPLE 11 cis-(4,6,7-Trimethyl-2,3,3a,8a-tetrahydro-1H-8-oxacyclopenta[a]indene-5-yl) benzoate (I: R$^1$=R$^2$=R$^3$=Me, X=benzoyl, A+B=ethylene, n=1)

To a solution of 2.18 g (10 mmoles) of the product prepared according to Example 2 in 25 ml of anhydrous pyridine 1.6 g (11.4 mmoles) of benzoyl chloride is added, and the reaction mixture is stirred at room temperature for 24 hours. Then it is poured onto 150 g of crushed ice, extracted three times with ether, the ether extracts are combined, washed with 2% hydrogen chloride, dried over magnesium sulfate, the solvent is distilled off and the residue is recrystallized from methanol. Thus 2.8 g (87%) of white crystalline product are obtained.

M.p.: 119°–120° C.

$^1$H-NMR (CDCl$_3$):1.55–1.98 (5H, m, 3CH$_2$), 2.03 (3H, s, CH$_3$), 2.07 (3H, s, CH$_3$), 2.1 (1H, m, CH$_2$) 2.11 (3H, s, CH$_3$), 3.80 (1H, t-m, CH), 5.27 (1H, m, C—O), 7.53 (2H, t-m, aromatic pr.), 7.65 (2H, t-m, aromatic pr.), 8.25 (2H, m, aromatic pr.).

EXAMPLE 12

Diisopropyl-[2-(cis-4,6,7-trimethyl-2,3,3a,8a-tetrahydro-1H-8-oxacyclopenta[a]indene-5-yloxy)-ethyl]-amine hydrochloride (I: $R^1=R^2=R^3$=Me, X=i-$Pr_2$N—$CH_2$—$CH_2$—, A+B=ethylene, n=1)

2.0 g (9.2 mmoles) of the substance prepared according to Example 2 are dissolved in the mixture of 50 ml of dioxane and 20 ml of diethyl ether, and 2.4 g (12.1 mmoles) of 2-diisopropylaminoethyl chloride hydrochloride and 1.2 g (30 mmoles) of powdered sodium hydroxide are added to the thus-obtained solution. The reaction mixture is stirred at 45° C. for 6 hours, cooled to room temperature, washed with water, dried over magnesium sulfate, and the solvent is distilled off. The residue is dissolved in chloroform, anhydrous hydrogen chloride gas is introduced to it and the solvent is distilled off. The residual substance is recrystallized from a mixture of acetone and ether. Thus 1.9 g (54%) of white crystalline product is obtained.

M.p.: 148°–150° C.

$^1$H-NMR (CDCl$_3$): 1.52 (6H, d, J=6 Hz, 2CH$_3$), 1.58 d, (6H, d, J=6 Hz, 2CH$_3$), 1.6–2.0 (6H, m, 3CH$_2$), 2.03 (3H, s, CH$_3$), 2.12 (3H, s, CH$_3$), 2.19 (3H, s, CH$_3$), 3.35 (2H, m, 2N—CH), 3.75 (3H, CH$_2$—N and CH, 4.26 (2H, m, CH$_2$—O) 5.22 (1H, m, CH—O), 11.68 (1H, s, NH).

EXAMPLE 13 cis-1-[2-4,6,7-Trimethyl-2,3,3a,8a-tetrahydro-1H-8-oxacyclopenta[a]indene-5-yloxy)-ethyl]-piperidine hydrochloride (I: $R^1=R^2=R^3$=Me, X=2-(1-piperidyl)-ethyl, A+B=ethylene, n=1)

To a solution of 2.0 g (9.2 mmoles) of the compound prepared according to Example 2 in 50 ml of anhydrous dimethylformamide 0.96 g of 50% sodium hydride is added, the mixture is stirred for 10 minutes and then 1.87 g (10 mmoles) of 1-(2-chloro-1-ethyl)-piperidine hydrochloride is added to it. The reaction mixture is stirred at room temperature for 36 hours, poured onto 300 ml of water and extracted five times with ether. The ether extracts are combined, dried over magnesium sulfate, the solvent is distilled off, the residue is dissolved in chloroform and anhydrous hydrogen chloride gas is introduced to it. The chloroform is distilled off and the residue is recrystallized from acetone. Thus 1.8 g (53%) of white crystalline product is obtained.

M.p.: 201°–203° C.

$^1$H-NMR (CDCl$_3$): 1.4–1.6 (2H, m, 2'-CH$_2$), 1.6–1.8 (3H, m, 1'-CH$_2$ and 3H of 3-CH), 1.8–2.0 (4H, m, 2CH$_2$; 4 and 5 CH$_2$ of the piperidine ring), 2.05 (3H, s, C7-CH$_3$), 2.08 (1H, m, one H of 3'-CH$_2$), 2.13 (3H, s, C6-CH$_3$), 2.21 (3H, s, C4-CH$_3$), 2.35 (2H, m, CH$_2$, position 3 of the piperidine ring), 2.93 (2H, m, N-CH$_2$ piperidine ring), 3.40 (2H, t, J=5 Hz, N-CH$_2$ piperidine ring), 3.73 (3H, m, C3-H and N-CH$_2$ in the ethyl group), 4.23 (2H, m, O—CH$_2$), 5.22 (1H, m-t, CH—O), 12.46 (1H, s, NH+).

EXAMPLE 14 cis-4-[2-(4,6,7-Trimethyl-2,3,3a,8a-tetrahydro-1H-8-oxacyclopenta[a]indene-5-yloxy)-ethyl]-morpholine hydrochloride (I: $R^1=R^2=R^3$=Me, X=2-(4-morpholinyl)-ethyl, A+B=ethylene, n=1)

To a solution of 2.0 g (9.2 mmoles) of the product prepared according to Example 2 in 50 ml of anhydrous dimethylformamide 0.96 g (20 mmoles) of 50% sodium hydride is added, the mixture is stirred for 15 minutes, and then 1.8 g (9.7 mmoles) of 2-(4-morpholinyl)-ethyl chloride hydrochloride is added to it. The reaction mixture is stirred at room temperature for 36 hours, poured onto 300 ml of water and extracted with ether. The ether solution is dried over magnesium sulfate, the solvent is distilled off, the residue is dissolved in chloroform and anhydrous hydrogen chloride gas is introduced to the solution. The chloroform is distilled off, the residue is dissolved in the mixture of 60 ml of carbon tetrachloride and 2 ml of ethyl alcohol under heating and 20 ml of hexane are added to it. The separated crystalline product is filtered and washed with hexane. Thus 1.6 g (47%) of white crystalline product is obtained.

M.p.: 175°–176° C.

$^1$H-NMR (CDCl$_3$): 1.54 (1H, m, one H of 3'-CH$_2$), 1.6–1.8 (3H, m, three H of 1'- and 2'-CH$_2$), 1.8–2.0 (1H, m, one H of 1'- and 2'-CH$_2$), 2.06 (3H, s, C7-CH$_3$), 2.08 (1H, m, one H of 3'-CH$_2$), 2.13 (3H, s, C6-CH$_3$), 2.21 (3H, s, C4-CH$_3$), 3.18 (2H, s, CH$_2$-N), 3.48 (2H, m-t, CH$_2$-N), 3.70 (1H, bs, C3-H), 3.72 (2H, m-t, CH$_2$-N), 4.02 (2H, m-d, CH$_2$O), 4.27 (2H, m, O—CH$_2$), 4.35 (2H, m-t, CH$_2$-O), 5.22 (1H, m-t, CH—O), 13.42 (1H, bs, NH+).

EXAMPLE 15 cis-1-[2-(6,7-Dimethyl-2,3,3a,8a-tetrahydro-1H-8-oxacyclopenta[a]indene-5-yloxy)-ethyl]-piperidine hydrochloride (I: $R^1=R^2$=Me, $R^3$=H, X=2-(1-piperidyl)-ethyl, A+B=ethylene, n=1)

To a solution of 2.04 g (10 mmoles) of the compound prepared according to Example 4 in 50 ml of anhydrous dimethylformamide 1.1 g (22.9 moles) of 50% sodium hydride is added, and the mixture is stirred for 15 minutes. Then 2.05 g (11 mmoles) of 1-(2-chloro-1-ethyl)-piperidine hydrochloride are added to it, the mixture is stirred at room temperature for 24 hours, poured onto 300 ml of water and extracted five times with ether. The ether extracts are combined, dried over magnesium sulfate, the solvent is distilled off, the residue is dissolved in anhydrous ether and hydrochloride salt is formed by introducing hydrogen chloride gas to the solution. The separated crystals are filtered off and washed with anhydrous ether. Thus 1.75 g (50%) of white crystalline product is obtained. M.p.: 202°–203° C.

$^1$H-NMR (CDCl$_3$): 1.46 (2H, m, CH$_2$), 1.6–1.95 (8H, m, 4CH$_2$), 2.06 (3H, s, CH$_3$), 2.097 (3H, s, CH$_3$), 2.28 (2H, m, CH$_2$), 2.86 (2H, m, CH$_2$-N), 3.42 (2H, m, CH$_2$-N), 3.67 (2H, m, CH$_2$-N), 3.79 (2H, m-t, J=7 Hz, CH$_2$-N), 4.45 (2H, m-q, CH$_2$-O), 5.215 (1H, m, CH—O), 6.55 (1H, s, aromatic pr.), 12.4 (1H, bs, NH).

EXAMPLE 16 cis-(4,6,7-Trimethyl-3a,8a-dihydro-1H-8-oxacyclopenta[a]indene-5-yl) acetate (I: $R^1=R^2=R^3$=Me, X=Ac, A+B=vinylene, n=1)

To a solution of 4.0 g (18.5 mmoles) of the product prepared according to Example 1 in 20 ml of anhydrous pyridine 3 ml (32 mmoles) of acetic anhydride are added, and the mixture is stirred at room temperature for 6 hours. Then it is poured onto the mixture of 100 g of ice and 3.5 ml of concentrated hydrochloric acid, the separated crystals are filtered off, washed with water and recrystallized from methanol. Thus 0.8 g (17%) of white crystalline product is obtained.

M.p.: 92°–93° C.

$^1$H-NMR (CDCl$_3$): 1.98 (3H, s, CH$_3$), 2.02 (3H, s, CH$_3$), 2.08 (3H, s, CH$_3$), 2.10 (3H, s, CH$_3$), 2.45–3.0 (2H, m, CH$_2$), 4.0 (1H, m, CH), 5.75 (1H, m, CH—O), 5.95 (2H, m, CH=CH).

EXAMPLE 17 cis-(4,6,7-Trimethyl-2,3,3a,8 a-tetrahydro-1H-8-oxacyclopenta[a]indene-5-yl) acetate (I: $R^1=R^2-R^3$=Me, X=Ac, A+B=ethylene, n=1)

A solution of 2.98 g (11.6 moles) of the substance prepared as specified in Example 16 in 150 ml of anhydrous methanol is hydrogenated using 0.5 g of 5% palladium on charcoal catalyst. When the calculated amount of hydrogen (280 ml, 30 minutes) has been taken up the catalyst is filtered off, the solvent is distilled off and the residue is recrystallized from anhydrous methanol. Thus 2.4 g (80%) of white crystalline product are obtained.

$^1$H-NMR (CDCl$_3$): 1.5–1.95 (5H, m, 2 CH$_2$ and one H of CH$_2$), 1.99 (3H, s, CH$_3$), 2.04 (3H, s, CH$_3$), 2.08 (3H, s, CH$_3$), 2.10 (1H, m, one H of CH$_2$), 2.32 (3H, s, CH$_3$), 3.755 (1H, t+d, J=6 Hz and 2 Hz, CH), 5.235 (1H, m, CH—O).

EXAMPLE 18 cis-(6-Methoxy-2,3,3a,8a-tetrahydro-1H-8-oxacyclopenta[a]indene-5-yl) benzoate (I: R$^1$=MeO, R$^2$=R$^3$=H, X=benzoyl, A+B=ethylene, n=1)

To a solution of 2.1 g of the product prepared according to Example 6 in 10 ml of anhydrous pyridine 1.7 g (12 mmoles) of benzoyl chloride is added, and the mixture is stirred at room temperature for 10 hours. Then it is poured onto the mixture of 30 g of crushed ice and 8 ml of hydrochloric acid, the separated white crystalline product is filtered off, washed with water, dried and recrystallized from ethanol. Thus 2.8 g (90%) of white crystalline product are obtained. M.p.: 138° C.

$^1$H-NMR (CDCl$_3$): 1.55 (1H, m, CH$_2$), 1.65–1.9 (4H, m, 2CH$_2$), 2.07 (1H, m, dd, CH$_2$), 3.74 (3H, s, CH$_3$O), 3.82 (1H, m-t, J=8 Hz, CH), 5.3 (1H, m-t, O—CH), 6.42 (1H, s, aromatic pr.), 6.88 (1H, s, aromatic pr.), 7.48 (2H, m, aromatic pr.), 7.6 (1H, m, aromatic pr.), 8.2 (2H, m, aromatic pr.).

EXAMPLE 19 cis-(4,6,7-Trimethyl-2,3,3a,8a-tetrahydro-1H-8-oxacyclopenta[a]indene-5-yl)-(3,4,5-trimethoxybenzoate) (I: R$^1$=R$^2$=R$^3$=Me, X=3,4,5-trimethoxybenzoyl, A+B=ethylene, n=1)

To a solution of 1.9 g (9 mmoles) of the product prepared according to Example 2 in 30 ml of anhydrous pyridine 2.45 g of 3,4,5-trimethoxybenzoyl chloride are added, and the mixture is stirred at room temperature for 15 hours. Then it is poured onto water, the separated precipitate is filtered off, washed with water and recrystallized from methanol. Thus 3.1 g (83.8%) of the desired product are obtained.

$^1$H-NMR (CDCl$_3$): 1.1–1.95 (5H, m, 3CH$_2$), 2.03 (3H, s, CH$_3$), 2.08 (3H, s, CH$_3$), 2.13 (3H, s, CH$_3$), 2.14 (1H, m, CH$_2$), 3.8 (1H, m-t, CH), 3.95 (9H, s, 3OCH$_3$), 5.28 (1H, m, CH—O), 7.5 (s, aromatic pr.).

EXAMPLE 20

Diethyl-[2-(cis-6,7-dimethyl-2,3,3a,8-tetrahydro-1H-8-oxacyclopenta[a]indene-5-yloxyethyl]-amine hydrochloride (I: R$^1$=R$^2$=Me, R$^3$=H, X=Et$_2$N-CH$_2$-CH$_2$, A+B=ethylene, n=1)

To a solution of 2.5 g (12 moles) of the compound prepared according to Example 4 in 40 ml of anhydrous dioxane 1.3 g (50% oily suspension, 27 moles) of sodium hydride is added in small portions, and the mixture is stirred for 1.5 hours. Then 2.34 g (13.5 moles) of the hydrochloride salt of 2-(diethylamino)-ethyl chloride are added to it, and the reaction mixture is stirred at room temperature for 48 hours. The solvent is distilled off in vacuo, the residue is taken up in 100 ml of ether, washed with water, dried and gaseous hydrogen chloride is introduced to it. The ether is decanted from the separated precipitate and the residue is recrystallized from ethyl methyl ketone. Thus 1.5 g of white crystalline product is obtained.

M.p.: 128°–130° C.

$^1$H-NMR (CDCl$_3$): 1.48 (6H, t, J=7 Hz, 2CH$_3$), 1.5–2.0 (5H, m, CH$_2$), 2.05 (1H, m, CH$_2$), 2.07 (3H, s, CH$_3$), 2.10 (3H, s, CH$_3$), 3.29 (4H, m, 2 N-CH$_2$), 3.80 (1H, m-t, J=7 Hz and 1.5 Hz, CH), 4.42 (2H, m, O—CH$_2$), 5.22 (1H, m, J=7 Hz and 1.5 Hz, CH), 6.52 (1H, s, aromatic pr.), 12.8 (1H, br s., NH$^+$).

EXAMPLE 21 cis-4,6-Dimethoxy-3a,8a-dihydro-3H-8-oxacyclopenta[a]indene-5-ol (I: R$^1$=R$^3$=MeO, R$^2$=X=H, A+B=vinylene, n=1)

To a solution of 5.0 g (29 mmoles of 2,6-dimethoxyhydroquinone (II: R$^1$=R$^3$=MeO, R$^2$=R$^4$=H) and 3.5 g (29 mmoles) of cis-4-cyclopentene-1,3-diol (III: n=1) in 30 ml of anhydrous toluene 0.5 g of p-toluenesulfonic acid is added, and the reaction mixture is stirred at a temperature of 70° C. for 3 hours. Then it is cooled, diluted with 200 ml of ethyl acetate, washed with water and saturated sodium chloride solution, dried and the solvent is distilled off. The residue is purified by column chromatography (Kieselgel G., hexane:acetone 10:1) and crystallized from hexane. Thus 1.29 g (21%) of light yellow crystalline product is obtained.

M.p.: 140° C.

$^1$H-NMR: 2.67 and 2.80 (2H, m, CH$_2$), 3.80 (3H, s, OCH$_3$), 3.96 (3H, s, OCH$_3$), 4.16 (1H, dd, J=8 and 2.5 Hz, CH), 5.11 (1H, s, OH), 5.78 (1H, dd, J=8 and 2.5 Hz, CH—O), 5.80 (1H, m, CH=), 6.00 (1H, m, CH=), 6.16 (1H, s, aromatic pr.).

EXAMPLE 22 cis-6-Propyloxy-3a,8a-dihydro-3H-8-oxacyclopenta[a]indene-5-ol (I: R$^1$=PrO, R$^2$=R$^3$=X=H, A+B=vinylene, n=1)

To a suspension of 5.0 g (22 mmoles) of 2,5-dipropoxyhydroquinone (II: R$^1$=R$^4$=PrO, R$^2$=R$^3$=H) and 2.4 g (24 mmoles) of cis-4-cyclopentene-1,3-diol (III: n=1) in 50 ml of anhydrous toluene 0.2 g of D-camphor-10-sulfonic acid is added, and the mixture is stirred under nitrogen atmosphere at a temperature of 65° C. for 30 hours. The separated precipitate is filtered off, the filtrate is evaporated and the residue is purified by column chromatography. Thus 0.7 g (28%) of white crystalline substance is obtained.

M.p.: 69° C.

$^1$H-NMR (CDCl$_3$): 1.02 (3H, t, J=6.5 Hz, CH$_3$), 1.8 (2H, sexst., J=6.5 Hz, CH$_2$), 2.54 and 2.86 (2H, m, CH$_2$), 3.91 and 3.94 (2H, m, CH2-O), 4.00 (1H, m, CH), 5.28(1H, s, OH), 5.78 (1H, m, CH—O), 5.82 (1H, m, CH=), 6.00(1H, m, CH=), 6.37 (1H, s, aromatic pr.), 6.73 (1H, s, aromatic pr.).

EXAMPLE 23 cis-1,3,4-Trimethyl-5a,8,9,9a-tetrahydrodibenzofurane-2-ol (I: R$^1$=R$^2$=R$^3$=Me, X=H, A+B=vinylene, n=2)

To a solution of 5.0 g (33 mmoles) of trimethylhydroquinone (II: R$^1$=R$^2$=R$^3$=Me, R$^4$=H) and 5.0 g (44 mmoles) of cis-2-cyclohexen-1,4-diol (III: n=2) in 100 ml of anhydrous toluene 1.0 g of D-camphor-10-sulfonic acid is added, and the mixture is stirred at a temperature of 70° C. for 40 hours. Then it is cooled, diluted with 100 ml of ether, washed twice with water and once with saturated sodium chloride solution, dried and the solvent is distilled off. The residue is purified by column chromatography (Kieselgel G, hexan:ether 1:1) and recrystallized from hexane. Thus 2.0 g (25.74%) of white crystalline product are obtained, M.p.: 122°–123° C.

$^1$H-NMR (CDCl$_3$): 1.34 (1H, m, one H of CH$_2$), 1.8–2.6 (3H, m, CH$_2$ and one H of CH$_2$), 2.11 (6H, s, 2CH$_3$), 2.18 (3H, s, CH$_3$), 3.13 (1H, m, CH), 4.26 (1H, s, OH), 4.74 (1H, dd, J=7 and 2.5 Hz, CH—O), 6.12 (1H, m, CH=), 6.14 (1H, m, CH=).

EXAMPLE 24 cis-(4,6,7-Trimethyl-3a,8a-dihydro-1H-8-oxacyclopenta-[a] indene-5-yl)-(4-nitrobenzoate) (I: R$^1$=R$^2$=R$^3$=Me, X=4-nitrobenzoyl, A+B=vinylene, n=1)

To a solution of 5.0 g (23 mmoles) of the substance prepared according to Example 1 in 50 ml of anhydrous pyridine 4.5 g (24 mmoles) of 4-nitrobenzoyl chloride are added, and the reaction mixture is stirred at room temperature for 10 hours. Then it is added to a mixture of 2N hydrochloric acid and crushed ice, the separated crystals are filtered off, washed with water and recrystallized from ethanol. The separated crystalline product is recrystallized four times from acetone. Thus 1.0 g (11.8%) of yellow crystalline product is obtained.

M.p.: 170°–173° C.

$^1$-NMR (CDCl$_3$): 2.02 (3H, s, CH$_3$), 2.08 (3H, s, CH$_3$), 2.12 (3H, s, CH$_3$), 2.55 (1H, m, one H of CH$_2$), 2.93 (1H, m, one H of CH$_2$), 4.13 (1H, t-m, J=4 Hz, CH), 5.86 (1H, d-m, J=4 Hz, CH—O).

EXAMPLE 25 cis-(6,7-Dimethyl-3a,8a-dihydro-3H-8-oxacyclopenta[a] indene-5-yl) benzoate (I: R$^1$=R$^2$=Me, R$^3$=H, X=benzoyl, A+B=vinylene, n=1)

To a solution of 2.65 g (13 moles) of the substance prepared according to Example 3 in 15 ml of anhydrous pyridine 1.92 g (1.6 ml, 14 moles) of benzoyl chloride is added, and the mixture is stirred at room temperature for 15 hours. Then it is poured onto a mixture of 50 g of ice and 5 ml of hydrochloric acid, the separated solid substance is filtered off and recrystallized from ethanol. Thus 2.2 g (55%) of white crystalline product are obtained.

$^1$H-NMR (CDCl$_3$): 2.05 (3H, s, CH$_3$), 2.15 (3H, s, CH$_3$), 2.56 (1H, m, one of CH$_2$), 2.9 (1H, m, dd, one H of CH$_2$), 4.08 (1H, m-t, CH), 5.8–5.9 (2H, m, CH and CH=), 6.8 (1H, s, aromatic pr.), 7.5 (2H, m, aromatic pr.), 7.64 (1H, m, aromatic pr.), 8.22 (2H, m, aromatic pr.).

EXAMPLE 26

3-Ethoxy-5a,8,9,9a-tetrahydrodibenzofurane-2-ol (I: R$^2$=R$^3$=X=H, R$^1$=EtO, A+B=vinylene, n=2)

To a solution of 20.7 g (0.1 moles) of 2-ethoxyhydroquinone and 0.8 g of p-toluenesulfonic acid in 200 ml of toluene 12.9 g (0.11 moles) of 2-cyclohexan-1, 4-diol (III: n=2) are added, and the mixture is stirred at a temperature of 70° C., under nitrogen atmosphere for 24 hours. Then it is filtered, the filtrate is evaporated, the residue is purified by column chromatography and recrystallized from hexane. Thus 3.3 g (14.1%) of the desired product are obtained.

M.p.: 92°–94° C.

$^1$H-NMR (CDCl$_3$): 1.41 (3H, t, J=7 Hz, CH$_3$), 1.55 (1H, m, CH$_2$), 1.9 (2H, m, CH$_2$), 2.1 (1H, m, CH$_2$), 3.31 (1H, m, CH), 4.04 (2H, q, J=7 Hz, CH$_2$), 4.95 (1H, m, CH), 5.3 (1H, s, OH), 5.92 (1H, m, CH=), 6.11 (1H, m, CH=), 6.4 (1H, s, arom. H), 6.77 (1H, s, arom. H).

EXAMPLE 27 cis-1,3,4-Trimethyl-5a,6,7,8,9,9a-hexahydrodibenzofurane-2-ol (I: R$^1$=R$^2$=R$^3$=Me, A+B=ethylene, X=H, n=2)

To a solution of 3.0 g (19.7 mmoles) of trimethyl hydroquinone (II: R$^1$=R$^2$=R$^3$=Me) and 3.16 g (39.5 mmoles) of 1,3-cyclohexadiene (IV: n=2) in 70 ml of toluene 0.6 g (3.4 mmoles) of p-toluenesulfonic acid is added, and the mixture is kept at 100° C. for 15 minutes. Then it is cooled, diluted with 150 ml of ether, extracted with 10% sodium hydrogen carbonate solution and water, dried, the solvent is distilled off and the residue is crystallized from a mixture of methanol and hexane. Thus 3.4 g (43%) of white crystalline product are obtained.

M.p.: 115°–118° C.

$^1$H-NMR (CDCl$_3$): 1.1 and 1.22 (2H, m, CH$_2$), 1.65 (4H, m, 2CH$_2$), 1.92 (1H, m, CH), 2.13 (3H, s, CH$_3$), 2.14 (3H, s, CH$_3$), 2.153 (3H, s, CH$_3$), 2.59 (1H, m, CH), 2.96 (1H, m, CH), 4.2 (1H, s, OH), 4.46 (1H, m, CH—O).

EXAMPLE 28 cis-1,3-Dimethoxy-5a,6,7,8,9,9a-hexahydrodibenzofurane-2-ol (I: R$^1$=R$^3$=MeO, R$^2$=H, A+B=ethylene, X=H, n=2)

To a solution of 1.7 g (10 mmoles) of 2,6-dimethoxyhydroquinone (III: R$^1$=R$^3$=MeO, R$^2$=H) and 1.5 g (19 mmoles) of 1,3-cyclohexadiene (IV: n=2) in 30 ml of toluene 1.9 g of p-toluenesulfonic acid are added, and the mixture is stirred first at 70° C. for 15 hours and then at 100° C. for 5 hours. The reaction mixture is then cooled, diluted with 30 ml of ether, washed with water and saturated sodium chloride solution, dried and the solvent is distilled off. The residue is purified by column chromatography. Thus 0.9 g (36%) of white crystalline product is obtained.

M.p.: 97°–98° C.

$^1$H-NMR (CDCl$_3$): 1.2–2.1 (8H, m, CH$_2$), 3.1 (1H, m, CH), 3.78 (3H, s, OCH$_3$), 3.95 (3H, s, OCH$_3$), 4.55 (1H, m, CH—O), 5.2 (1H, bs, OH), 6.2 (1H, s, aromatic pr.).

EXAMPLE 29 cis-1,2-Dimethyl-4b,6,7,8,9,9a-hexahydro-5H-10-oxabenzo[a]azulene-3-ol (I: R$^1$=R$^2$=Me, R$^3$=H, A+B=ethylene, X=H, n=3)

To a solution of 2.0 g (14 mmoles) of 2,3-dimethylhydroquinone (II: R$^1$=R$^2$=Me, R$^3$=R$^4$=H), and 1.63 g (17 mmoles) of 1,3-cycloheptadiene (IV: n=3) in 50 ml of anhydrous toluene 0.2 g of p-toluenesulfonic acid is added, and the mixture is stirred at a temperature between 70° C. and 80° C. for 18 hours. Then it is cooled, diluted with 100 ml of ether, washed with water and saturated sodium chloride solution, the solvent is distilled off and the residue is purified by column chromatography. Thus 1.2 g (37%) of white crystalline product is obtained.

M.p.: 105°–107° C.

$^1$H-NMR (CDCl$_3$): 1.3–2.0 (8H, m, 4CH$_2$), 2.12 (6H, s, 2CH$_3$), 2.4 (2H, m, CH$_2$), 2.85 (1H, m, CH), 4.2 (1H, m, OH), 4.8 (1H, m, CH—O), 6.4 (1H, s, aromatic pr.).

We claim:

1. Oxaindene derivatives of formula (1).

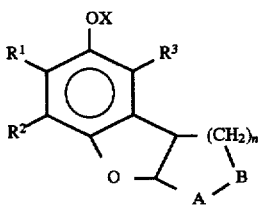

wherein

R¹ represents lower $C_{1-4}$ alkyl, lower $C_{1-4}$ alkoxy or lower $C_{3-6}$ cycloalkyl, R² stands for hydrogen, lower $C_{1-4}$ alkyl or lower $C_{3-6}$ cycloalkyl, R³ stands for hydrogen, lower $C_{1-4}$ alkyl, lower $C_{1-4}$ alkoxy or benzyloxy, X denotes hydrogen, an aliphatic $C_{1-4}$-acyl or benzoyl or naphthoyl group, optionally substituted by 1 or more nitro or $C_{1-4}$-alkoxy group(s) or a group of the formula $R^5R^6N—R^7—$, wherein R⁷ represents lower $C_{1-4}$ alkylene and R⁵ and R⁶ each represent lower $C_{1-4}$ alkyl, or R⁵ and R⁶ together with the nitrogen atom to which they are attached form a piperidyl or morpholinyl group, A and B together form an ethylene or a vinylene group, and n is 1, 2 or 3, stereoisomers and pharmaceutically acceptable acid addition salts thereof.

2. Compounds as claimed in claim 1, wherein R¹ represents lower alkyl, R² and R³ represent independently hydrogen, lower alkyl, X stands for hydrogen, A and B together represent vinylene and n is 1 or 2.

3. Compounds as claimed in claim 1, wherein R¹ represents lower alkyl, R² and R³ represent independently hydrogen, lower alkyl, X stands for hydrogen, A and B together represent ethylene and n is 1 or 3.

4. .cis-4,6,7-Trimethyl-2,3,3a-8a-tetrahydro-1H-8-oxacyclopenta[a]indene-5-ol, 1,2,4-trimethyl-4b,6,7,8,9,9a-hexahydro-5H-10-oxabenzo[a]azulene-3-ol and cis-4,6,7-trimethyl-3a, 8a-dihydro-3H-8-oxacyclopenta[a]indene-5-ol.

5. A process for the preparation of the compounds of formula (I) according to claim 1, which comprises a) for the preparation of compounds of general formula (I), wherein A and B together form a vinylene group and R¹, R², R³, and X and n are as stated above, reacting a hydroquinone derivative of formula (II)

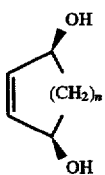

wherein R¹, R² and R³ are stated above and R⁴ represents hydrogen or lower alkoxy, with a cycloalkene derivative of formula (III),

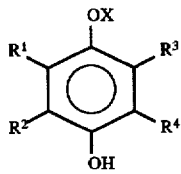

wherein n is as stated above, in a solvent, in the presence of the catalytic amount of a strong acid, and, if desired, subjecting the thus-obtained compound of formula (I), wherein X represents hydrogen, to acylation or dialkylaminoalkylation, or b) for the preparation of compounds of general formula (I), wherein A and B together form an ethylene group, b1) subjecting a compound of formula (I), wherein A and B together form a vinylene group, X stands for hydrogen and R¹, and R², and R³ and n are as stated above, to catalytic hydrogenation, or b2) reacting a hydroquinone derivative of formula (II), wherein R¹, R² and R³ are as stated above and R⁴ represents hydrogen, with a cycloalkadiene derivative of formula (IV)

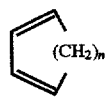

wherein n is as stated above, in a solvent, in the presence of the catalytic amount of a strong acid, and, if desired, subjecting the thus-obtained compound of formula (I) thus-obtained into an acid addition salt thereof.

6. A process according to variant a) of claim 5, which comprises carrying out the reaction in an aprotic solvent.

7. A process according to anyone of claims 5 and 6, wherein the strong acid employed in variant a) is selected from the group consisting of p-toluenesulfonic acid, camphor-10-sulfonic acid and benzenesulfonic acid.

8. A process according to variant a) of claim 5, which comprises carrying out the reaction at a temperature of between 60° C. and 110° C.

9. A process according to variant b1) of claim 5, which comprises carrying out the catalytic hydrogenation in a polar solvent.

10. A process according to any one of claims 5 and 9, wherein a catalyst for the hydrogenation employed in variant b1 palladium.

11. A process according to variant b1) of claim 5, which comprises carrying out the reaction at room temperature.

12. A process according to wherein the strong acid employed in variant b2) is selected from the group consisting of p-toluenesulfonic acid, camphor-10-sulfonic acid and benzenesulfonic acid.

13. A process according to variant b2) of any one of claims 5 and 12, which comprises carrying out the reaction in anhydrous aprotic solvent.

14. A process according to variant b2) of claim 5, which comprises carrying out the reaction at a temperature of between 30° C. and 90° C.

15. Process according to claim 6, wherein the aprotic solvent is an aromatic hydrocarbon.

16. The process according to claim 6, wherein the reaction according to variant a) is carried out at a temperature of between 60° C. and 110° C.

17. The process according to claim 7, wherein the reaction according to variant a) is carried out at a temperature of between 60° C. and 110° C.

18. The process according to claim 9, wherein the reaction according to variant b1) is carried out at room temperature.

19. The process according to claim 10, wherein the reaction according to variant b1) is carried out at room temperature.

20. The process according to claim 12, wherein the reaction according to variant b2) is carried out at a temperature of between 30° C. and 90° C.

21. The process according to claim 13, wherein the reaction according to variant b2) is carried out at a temperature of between 30° C. and 90° C.

22. Pharmaceutical compositions comprising as active ingredient a compound of formula (I) according to claim 1 or a pharmaceutically acceptable acid addition salt thereof in admixture with suitable inert solid or liquid pharmaceutical carriers.

23. A method for treating allergies, diseases of the joints, gastrointestinal tract and skin disorders, which comprises administering to a patient an effective amount of a compound of formula (I) or a pharmaceutically acceptable acid addition salt thereof.

* * * * *